(12) United States Patent
VanDenBogart et al.

(10) Patent No.: US 9,339,419 B2
(45) Date of Patent: May 17, 2016

(54) TAMPON APPLICATOR

(75) Inventors: Tom William VanDenBogart, Slinger, WI (US); Cao Hue Chi Pham, Alpharetta, GA (US); Yein Sze Ong, Singapore (SG); Franz Aschenbrenner, Kastl (DE); Dušan Pavlík, Novy Jicin (CZ); Gary Mastalish, Oshkosh, WI (US); Irina Tsareva, Moscow Region (RU); Lynn Ann Weggel, Appleton, WI (US); Anastasia Barlas, Arncliffe (AU); Priscilla Eng Choo Goh, Maplewoods (SG); EunJung Kang, Seoul (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 2329 days.

(21) Appl. No.: 12/173,516

(22) Filed: Jul. 15, 2008

(65) Prior Publication Data

US 2010/0016780 A1    Jan. 21, 2010

(51) Int. Cl.
  *A61F 13/26*  (2006.01)

(52) U.S. Cl.
  CPC ............... *A61F 13/26* (2013.01); *A61F 13/266* (2013.01)

(58) Field of Classification Search
  CPC ............................ A61F 13/26; A61F 13/266
  USPC ....................................................... 604/11–18
  See application file for complete search history.

(56) References Cited

U.S. PATENT DOCUMENTS

| 2,489,502 | A |   | 11/1949 | Ruth |
|---|---|---|---|---|
| 3,042,040 | A |   | 7/1962 | Galik |
| 3,534,737 | A |   | 10/1970 | Jones, Sr. |
| 3,765,417 | A |   | 10/1973 | Crockford |
| 4,048,998 | A |   | 9/1977 | Nigro |
| D250,663 | S |   | 12/1978 | Koch |
| 4,198,978 | A |   | 4/1980 | Nigro |
| 4,361,150 | A |   | 11/1982 | Voss |
| 4,412,833 | A | * | 11/1983 | Wiegner et al. .................. 604/14 |

(Continued)

FOREIGN PATENT DOCUMENTS

| EP | 0115193 | 2/1989 |
|---|---|---|
| EP | 0392281 | 10/1990 |

(Continued)

OTHER PUBLICATIONS

Moss, Mark D., Sequential Coinjection Hot Runner, Kona Corporation.

(Continued)

*Primary Examiner* — Lynne Anderson
(74) *Attorney, Agent, or Firm* — Armstrong Teasdale LLP

(57) ABSTRACT

In a tampon applicator, an elongated barrel has an interior chamber for housing a tampon therein, a grip region generally adjacent an outer end of the barrel, a tip region generally adjacent an inner end of the barrel, and a central region extending longitudinally between the grip region and the tip region. A plunger extends into the barrel at the outer end thereof and is moveable relative to the barrel to expel the tampon from the barrel at its inner end. The outer surface of the barrel at the grip region has a different coefficient of friction than at the central region of the barrel. In other embodiments the coefficient of friction of the barrel outer surface at the central region is different from the coefficient of friction at the tip region.

24 Claims, 7 Drawing Sheets

(56) References Cited

U.S. PATENT DOCUMENTS

| | | | |
|---|---|---|---|
| 4,428,370 A | 1/1984 | Keely | |
| 4,447,222 A | 5/1984 | Sartinoranont | |
| 4,536,178 A | 8/1985 | Lichstein | |
| 4,620,534 A | 11/1986 | Zartman | |
| 4,891,042 A | 1/1990 | Melvin et al. | |
| 4,973,302 A * | 11/1990 | Armour et al. | 604/15 |
| 5,158,535 A | 10/1992 | Paul | |
| 5,279,541 A | 1/1994 | Frayman | |
| 5,389,067 A | 2/1995 | Rejai | |
| 5,437,628 A | 8/1995 | Fox | |
| 5,453,085 A | 9/1995 | Schoelling | |
| 5,519,930 A | 5/1996 | Sengstock | |
| 5,533,990 A | 7/1996 | Yeo | |
| 5,558,631 A * | 9/1996 | Campion et al. | 604/13 |
| 5,681,894 A | 10/1997 | Williams | |
| 5,702,553 A | 12/1997 | Iskra | |
| 5,709,652 A | 1/1998 | Hagerty | |
| 5,738,646 A * | 4/1998 | Fox et al. | 604/15 |
| 5,746,710 A | 5/1998 | Nielsen | |
| 5,788,663 A | 8/1998 | Igaue | |
| 5,788,664 A | 8/1998 | Scalise | |
| 5,931,803 A | 8/1999 | Jackson | |
| D415,565 S | 10/1999 | Hayes | |
| 6,019,744 A * | 2/2000 | Altdorf et al. | 604/16 |
| 6,095,999 A | 8/2000 | Jackson | |
| 6,416,488 B1 | 7/2002 | Jackson | |
| 6,450,985 B1 | 9/2002 | Schoelling | |
| 6,450,986 B1 | 9/2002 | Binner | |
| 6,511,452 B1 | 1/2003 | Rejai | |
| 6,533,748 B2 | 3/2003 | Buzot | |
| 6,572,577 B1 | 6/2003 | Binner | |
| 6,610,025 B2 | 8/2003 | Berg | |
| 6,645,136 B1 | 11/2003 | Zunker | |
| 6,652,477 B2 | 11/2003 | Karapasha | |
| 6,673,032 B2 | 1/2004 | Buzot | |
| 6,695,763 B2 | 2/2004 | Zunker | |
| D492,033 S | 6/2004 | Jarmon et al. | |
| 6,890,324 B1 | 5/2005 | Jackson | |
| 6,923,789 B2 | 8/2005 | Lemay | |
| 6,939,289 B2 | 9/2005 | Zunker | |
| D512,142 S | 11/2005 | Weber et al. | |
| D515,212 S | 2/2006 | Edgett | |
| 7,014,637 B1 | 3/2006 | Denti | |
| 7,044,928 B2 | 5/2006 | Lemay | |
| 7,081,110 B2 | 7/2006 | Karapasha | |
| 7,172,573 B1 | 2/2007 | Lamb | |
| 7,241,274 B2 | 7/2007 | Suga | |
| 7,250,129 B2 | 7/2007 | Williams | |
| D572,362 S | 7/2008 | Edgett et al. | |
| D602,588 S | 10/2009 | VanDenBogart et al. | |
| 2003/0105421 A1 | 6/2003 | Jarmon et al. | |
| 2003/0216680 A1 * | 11/2003 | Binner et al. | 604/15 |
| 2004/0054317 A1 | 3/2004 | Lemay | |
| 2004/0199102 A1 | 10/2004 | Lemay et al. | |
| 2005/0070839 A1 | 3/2005 | Jackson et al. | |
| 2005/0177091 A1 | 8/2005 | Jarmon et al. | |
| 2006/0258971 A1 * | 11/2006 | Chase et al. | 604/12 |
| 2007/0032758 A1 * | 2/2007 | Chase et al. | 604/12 |
| 2007/0156080 A1 | 7/2007 | Loyd et al. | |
| 2008/0004563 A1 | 1/2008 | Lemay et al. | |
| 2008/0033337 A1 | 2/2008 | Dougherty | |
| 2008/0119778 A1 | 5/2008 | Jorgensen et al. | |

FOREIGN PATENT DOCUMENTS

| | | |
|---|---|---|
| EP | 1198215 | 8/2005 |
| EP | 1551347 | 12/2007 |
| GB | 2166656 | 5/1986 |
| WO | 0100126 | 1/2001 |
| WO | 2007089306 | 8/2007 |
| WO | 2008019093 | 2/2008 |

OTHER PUBLICATIONS

Selden, R., Sandwich Injection Molding of Thermoplastics—A Literature Survey, Journal of Injection Molding Technology, Dec. 1997, vol. 1, No. 4.

Allan; Bevis; McCalla; Mubarak, Multi-Component Laminate Moulding, Wolfson Centre for Materials Processing, Brunel University, Uxbridge, U.K.

Stewart, Richard, Multicomponent Molding: In-Mold Techniques Eliminate Downstream Operations to Cut Costs and Boost Quality, Plastics Engineering: North America Cover Story, www.4spe.org, Jun. 2008.

Nguyen; Turcott; Derdouri; Ait Messaoud; Sanschagrin; Salamon; Koppi, Polymer Melt Flow Behavior in the Coinjection Molding Process, Industrial Materials Institute, National Council Canada; Ecole Polytechnique; Dow Chemical.

http://www.businesswire.com/portal/site/exxonmobil/index , ExxonMobil Chemical Introduces New Transparent and Translucent TPE Grades to Inspire Design, Jun. 10, 2008.

Hartwig, Molding and Optimization of Barrier Properties for Stretch-blow Molded Bottles, Krupp Corpoplast Maschinenbau GmbH, D-22145 Hamburg, Germany, 5 pages.

Selden, R., Coinjection Molding: Compatibilization of Polyamide-Polypropylene Sandwich Structures, Journal of Injection Molding Technology, Dec. 1998, vol. 2, No. 4, 10 pages, Molndal, Sweden.

International Search Report and Written Opinion for PCT/IB2009/053051, dated Mar. 2, 2010, 6 pages.

\* cited by examiner

TAMPON APPLICATOR

BACKGROUND

The present invention relates generally to tampon applicators.

Vaginal tampons are disposable absorbent articles sized and shaped (e.g., cylindrical) for insertion into a women's vaginal canal for absorption of body fluids generally discharged during the woman's menstrual period. Insertion of the tampon into the vaginal canal is commonly achieved using a tampon applicator that comes initially assembled with the tampon. The applicator, which is often made of plastic or cardboard, is disposable. Thus, after the applicator has been used to insert the tampon into the user's vaginal canal the applicator is discarded.

Tampon applicators are typically of a two-piece construction, including a barrel in which the tampon is initially housed and a plunger moveable telescopically relative to the barrel to push the tampon out of the barrel and into the vaginal canal. The barrel has a tip that generally retains the tampon within the barrel until pushed through the tip by the plunger. In normal use, the applicator and more particularly the barrel of the applicator is held by the user by gripping one portion of the barrel (e.g., toward the trailing or plunger end of the barrel) and inserting the barrel, tip end first, into the vaginal canal. The barrel is pushed partially into the canal so that a portion (e.g., toward the leading or exit end of the tampon barrel) is disposed within the vaginal canal and is contact with the walls lining the canal. The plunger is then used to push the tampon out through the tip of the barrel and into the canal. The plunger and barrel are then removed from the vaginal canal, leaving the tampon in place.

In such use, the barrel (and plunger) of the applicator comes into contact with different body parts and/or skin regions of the user, such as the tip and part of the barrel contacting the walls lining the vaginal canal, while the user's finger(s) contact the barrel (and plunger) to grip and hold the barrel and to operate the plunger. The ability of the user to have a secure grip on the applicator while allowing the applicator to comfortably slide into and out of the vaginal canal is thus an important factor in acceptance of the applicator.

There is need, therefore, for a tampon applicator that provides a soft feeling, increased comfort and secure handling to the user.

SUMMARY

In one aspect, a tampon applicator generally comprises an elongated barrel having an interior chamber for housing a tampon therein, an outer end and an inner end spaced longitudinally from the outer end. A plunger extends into the barrel at the outer end thereof and is moveable relative to the barrel to expel the tampon from the barrel at the inner end of the barrel. The barrel has at least two petals each having a base and extending longitudinally of the barrel to a tip of the petal wherein the petal tips define the longitudinal inner end of the barrel. The petals are configurable relative to each other and to the barrel from a closed configuration in which the petals generally close the inner end of the barrel and an opened position in which the petals are moved generally transversely outward to form an exit opening at the inner end of the barrel upon movement of the plunger to expel the tampon from the barrel at its inner end. Each petal has a length from its base to its tip, and the barrel has a cross-sectional dimension at the bases of the petals. A ratio of the length of the petal to the cross-sectional dimension of the barrel at the bases of the petals is in the range of about 1.0 to about 2.0.

In another aspect, a tampon applicator generally comprises an elongated barrel having an interior chamber for housing a tampon therein, an outer end and an inner end spaced longitudinally from the outer end. A plunger extends into the barrel at the outer end thereof and is moveable relative to the barrel to expel the tampon from the barrel at the inner end of the barrel. The barrel has a guide channel extending longitudinally therein adjacent the outer end of the barrel. The plunger extends through the guide channel into the interior chamber of the barrel. The guide channel has a cross-sectional dimension sized for a close fit relationship of the plunger in the guide channel. The guide channel further has a length, with a ratio of the length of the guide channel to the cross-sectional dimension thereof being in the range of about 1.0 to about 2.0.

In yet another aspect, a tampon applicator generally comprises an elongated barrel having an interior chamber for housing a tampon therein, an outer end, an inner end spaced longitudinally from the outer end, a grip region generally adjacent the outer end of the barrel, a tip region generally adjacent the inner end of the barrel, a central region extending longitudinally between the grip region and the tip region, and an outer surface. A plunger extends into the barrel at the outer end thereof and is moveable relative to the barrel to expel the tampon from the barrel at the inner end of the barrel. The outer surface of the barrel at the grip region has at least one of a different color and a different coefficient of friction than the central region of the barrel.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
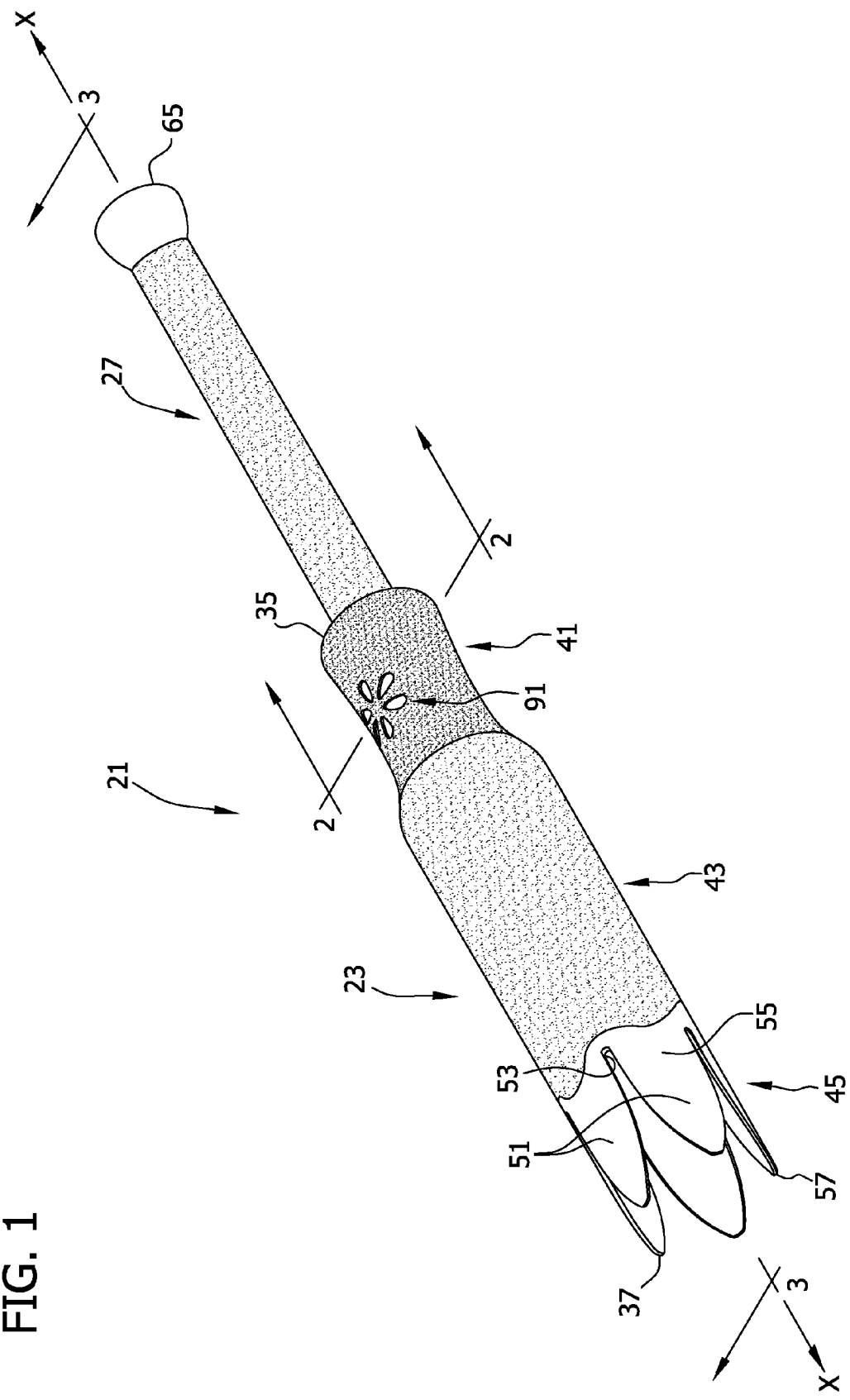
FIG. 1 is a perspective view of one embodiment of a tampon applicator with a plunger of the applicator illustrated in an extended position relative to a barrel of the applicator and with a tip of the barrel open to illustrate construction of the barrel.

Referring now to the drawings and in particular to FIG. 1, one embodiment of a tampon applicator is generally designated by reference numeral 21. The tampon applicator comprises a barrel, indicated generally at 23, housing a tampon 25 (FIG. 5), and a plunger, indicated generally at 27, moveable telescopically relative to the barrel to expel the tampon from the barrel. In the various embodiments herein the tampon applicator 21 is illustrated and described in connection with a vaginal tampon 25, i.e., a tampon such as a fibrous body sized and shaped (typically cylindrically shaped) for insertion into the vaginal canal of a female user to absorb menses, blood and other bodily fluids. It is understood, however, that the tampon applicator 21 may be used in connection with other suitable types of tampons. The tampon 25 includes a withdrawal string 29 (FIG. 5) fastened to the tampon generally adjacent an outer or trailing end 31 thereof for use in pulling the tampon from the vaginal canal. Suitable tampon 25 and withdrawal string 29 materials and constructions are known to those skilled in the art and are not further described herein except to the extent necessary set forth the present invention.

The tampon applicator 21 has a longitudinal axis X, with the barrel 23 and plunger 27 being in coaxial relationship with each other on this axis. The plunger 27 is thus moveable telescopically along the longitudinal axis X from an extended position as illustrated in FIG. 1 to a delivery position (not shown) to expel the tampon 25 from the barrel 23 of the applicator 21. It is understood, however, that the plunger 27 need not be coaxial with the barrel 23 and or the longitudinal axis X of the applicator 21 to remain within the scope of this invention.

The barrel 23 of the tampon applicator 21 is suitably sized and shaped for housing the tampon 25 within an interior chamber 33 (FIG. 3) of the barrel and for inserting the barrel into a body cavity of a user, such as the vaginal canal of a female user where the tampon is a vaginal tampon. The barrel 23 is generally elongated and also generally cylindrical, having an outer end 35, an inner end 37. The barrel 23 also broadly comprises a grip region 41 adjacent the outer end of the barrel, an intermediate or central region 43 longitudinally adjacent the grip region and at least in part defining the interior chamber 33 housing the tampon 25, and an exit or tip region 45 longitudinally adjacent the central region in longitudinally spaced relationship with the grip region. The terms inner end and outer end as used herein are referenced relative to the orientation of the tampon applicator 21 and its various components during use thereof, with the barrel 23 being inserted, inner end 37 first, into the body cavity (e.g., the vaginal canal).

Figure 3:
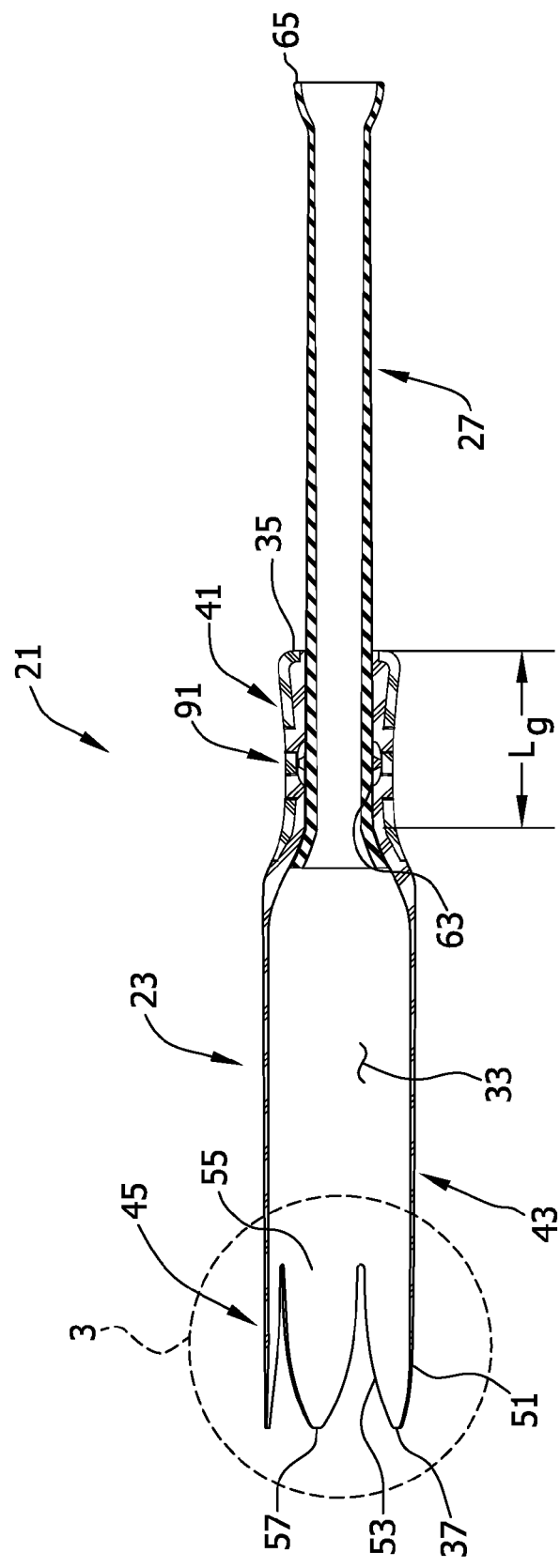
FIG. 3 is a longitudinal cross-section taken in the plane of line 3-3 of FIG. 1.
Figure 4:
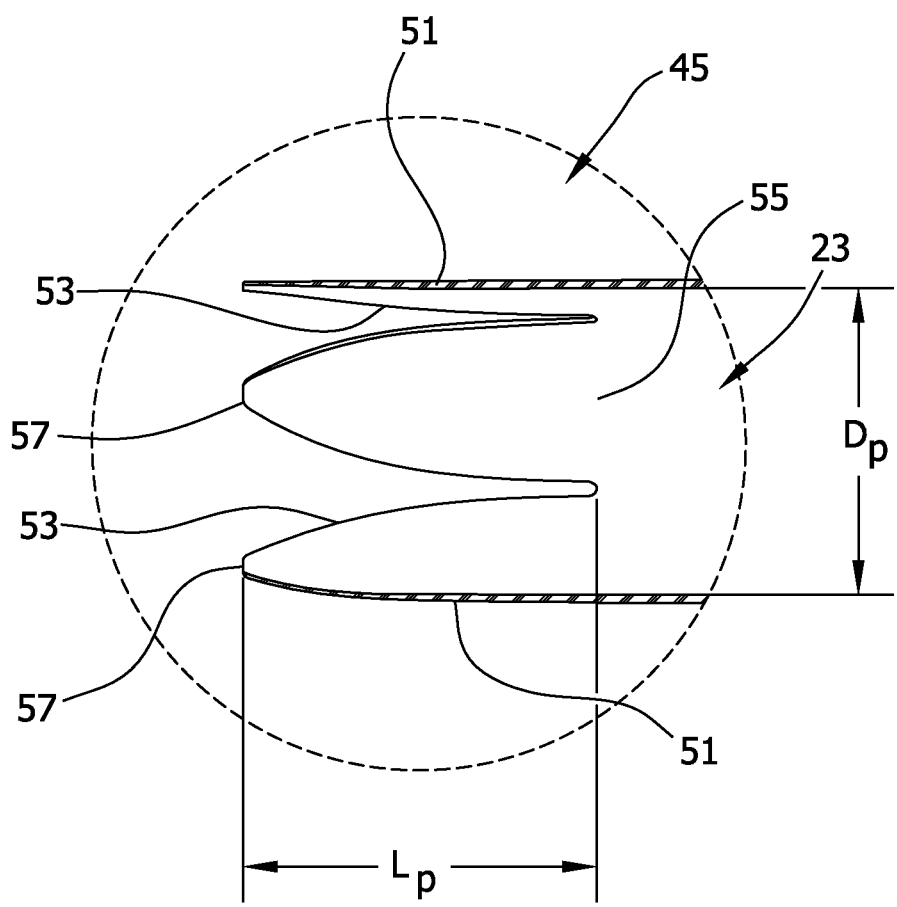
FIG. 4 is an enlarged view of a longitudinal segment of the applicator of FIG. 3.
Figure 5:
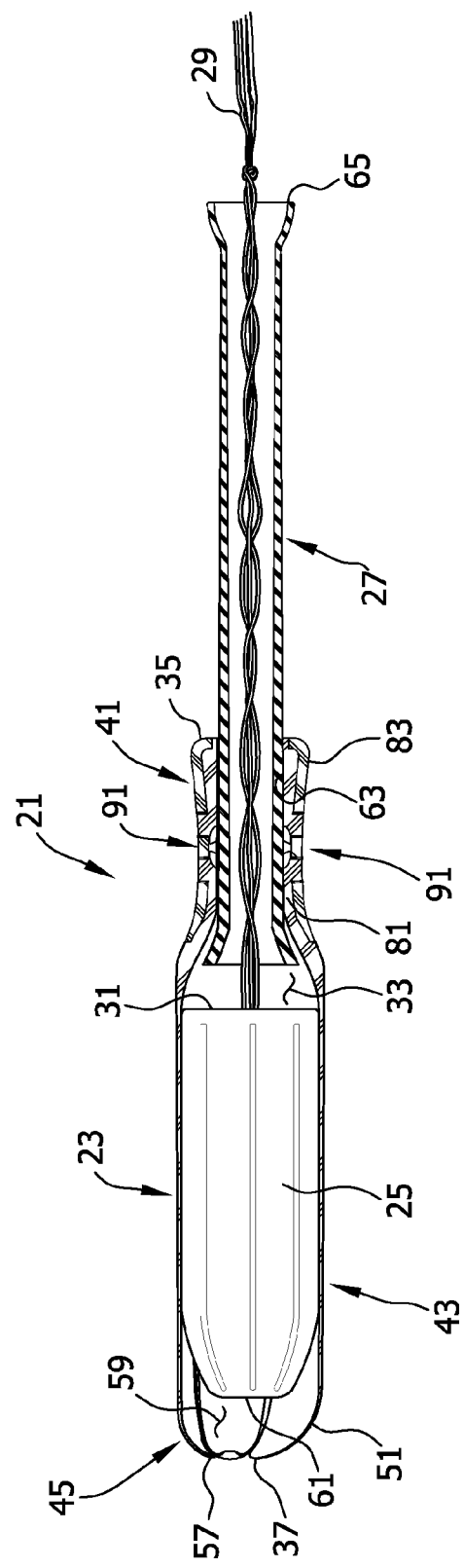
FIG. 5 is a longitudinal cross-section similar to FIG. 3 with the tip of the applicator barrel illustrated in its closed configuration.

With particular reference to FIGS. 3 and 4, the tip region 45 of the barrel 23 includes a plurality of extensions, or what is commonly referred to as petals 51, separated by longitudinal slots 53. Each of the petals 51 extends longitudinally from a base 55 of the petal 51, where the petal is connected to and is more suitably formed integrally with the rest of the barrel 25, to a free end or tip 57 of the petal. More suitably, the width of each petal tapers inward from its base 55 toward its tip 57. The petals 51 are suitably configured in this manner to permit the petals to be bent inward during manufacture of the applicator 21 as illustrated in FIG. 5 to generally close the barrel 23 at its inner end 37 to substantially enclose the tampon 25 in the interior chamber 33 of the barrel during packaging and storage (e.g., prior to use). The slots 53 allow for bending of the petals 51 into their closed configuration during manufacture, and for flexing or bending transversely (e.g., radially in the illustrated embodiment) outward upon application of force by the tampon 25 when the tampon is guided out of the barrel 23 by the plunger 27.

In one particularly suitable embodiment as illustrated in FIG. 4, the petals 51 are each sized in length Lp, e.g., as measured from the base 55 of the petal to its longitudinally furthest extent such as the tip 57 in FIG. 4, so that the petals are more readily flexed or bent transversely outward from their closed configuration to allow easier expulsion of the tampon 25 from the barrel 23 and to reduce the occurrences and strength of the petals pinching the user. For example, in one embodiment the length Lp of each petal 51 is in the range of about 10 mm to about 20 mm and is more suitably about 16 mm. In another embodiment, the applicator barrel 23 has an inner diameter Dp at the bases 55 of the petals 51, with the length Lp of the petals being at least equal to and more suitably greater than the inner diameter of the applicator barrel at the bases of the petals. For example, in a particularly suitable embodiment a ratio of the petal length Lp to the inner diameter Dp of the barrel 23 at the base 55 of the petals 51 is in the range of about 1.0 to about 2.0, more suitably in the range of about 1.0 to about 1.5, even more suitably in the range of about 1.0 to about 1.25, and most suitably about 1.1. As another example, in the illustrated embodiment the barrel 23 has an inner diameter Dp of about 14.5 mm at the bases 55 of the petals, and a petal length of about 15.8 mm, which provides a petal length to inner diameter ratio of about 1.1.

Such a configuration allows the petals 51 to be bent inward to their closed configuration closer to the tips 57 of the petals, such as approximately the longitudinally outer one-third of each petal, as opposed to being bent nearer to or at their bases 55. This provides a softer and more flexible feel to the petals 51 in their closed configuration and also facilitates the formation of a gap 59 (FIG. 5) longitudinally between an inner end 61 of the tampon 25 and the tips 57 of the petals when the petals are in their closed configuration (in which the tips of the petals broadly define the inner end 37 of the barrel 23). For example, in one suitable embodiment the gap 59 between the inner end 61 of the tampon 25 and the inner end 37 of the barrel is in the range of about 0.1 mm to about 1.5 mm, more suitably about 0.1 mm to about 0.75 mm and even more suitably about 0.1 mm to about 0.4 mm. The portions of the petals 51 that form this gap 59 are thus more compressible and flexible (e.g., because of the lack of support or stiffness that would otherwise be provided by the tampon 25 absent such a gap), thereby enhancing the soft and flexible feeling of the tip region 45 of the barrel 23. It is understood, however, that the petals 51 at the tip region 45 of the barrel 23 may be sized other than as described above, including being sized so that no gap 59 is present, without departing from the scope of this invention.

In another embodiment, to further facilitate a more soft and flexible feel and appearance at the tip region 45, the petals 51 are configured to have a lower stiffness (i.e., resistance to bending) than the central region 43 of the barrel. More suitably, the petals 51 may be formed to have a thickness that is less than the thickness of the barrel 23 at the central region 43 to effect a lower stiffness. For example, the petals may have a thickness in the range of about 0.2 mm to about 0.8 mm while at the central region 43 the barrel may have a thickness of about 0.4 mm to about 1.2 mm. The reduced thickness of the petals 51 allows the petals to be more flexible and pliable to provide a soft, flexible feel and appearance. It is understood, however, that the thickness of the petals 51 and/or the central region 43 of the barrel 23 may be other than as set forth above.

Figure 2:
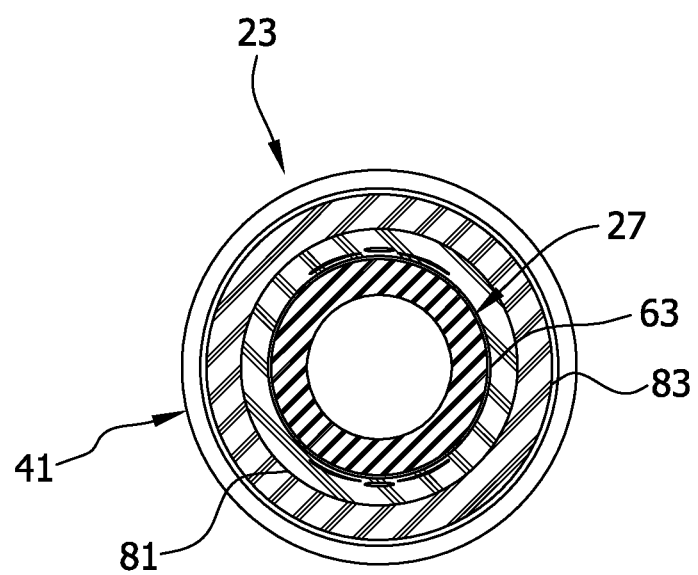
FIG. 2 is a transverse cross-section taken in the plane of line 2-2 of FIG. 1.

With reference back to FIGS. 2 and 3, the barrel 23 has an inner diameter (broadly, an inner cross-sectional dimension in the illustrated embodiment) adjacent the outer end 35 (e.g., at and/or adjacent the grip region 41) of the barrel 23. This inner diameter is substantially less than that along the central region 43 of the barrel 23 (i.e., the portion that at least in part defines the interior chamber 33 in which the tampon 25 is housed). This reduced diameter segment of the barrel 23 broadly defines a longitudinal guide channel 63 through which the plunger 27 extends and is supported by the barrel in coaxial (or at least longitudinal) relationship with the barrel.

In particular, the guide channel has an inner diameter sized for sliding friction fit with the plunger.

In one particularly suitable embodiment, the guide channel 63 has a length Lg sufficient to stably retain the plunger 27 coaxial with the barrel 23, i.e., to inhibit skewing of the plunger relative to the barrel as the plunger is pushed into the interior chamber 33 of the barrel to expel the tampon. For example, the length Lg of the guide channel 63 may suitably be in the range of about 5 mm to about 25 mm, more suitably in the range of about 12 mm to about 22 mm, and even more suitably about 15 mm to about 20 mm. As another example, the guide channel 63 of the applicator barrel 23 illustrated in FIG. 3 is approximately 18.6 mm in length. The length Lg of the guide channel 63, as used herein, refers to the longitudinal distance between the longitudinally innermost and outermost locations at which the inner diameter of the barrel 23 is sized for a close (e.g., relatively tight) fit and more suitably sliding friction contact with the plunger 27. Thus, it will be understood that the inner diameter of the barrel 23 may be substantially constant along the length Lg of the guide channel 63 as illustrated in FIG. 3, or the inner diameter may be sized approximately the same as an outer diameter of the plunger 27 at least at two longitudinally spaced locations, with the longitudinal spacing defining the length of the guide channel.

In another embodiment, a ratio of the guide channel 63 length Lg to the inner diameter of the barrel 23 segment that defines the guide channel is suitably in the range of about 1 to about 5, more suitably about 2 to about 4 and even more suitably about 3 to about 3.5. It is understood, however, that the inner diameter of the barrel 23 at the guide channel 63, and/or the guide channel length Lg, may be other than as set forth above without departing from the scope of this invention.

The plunger 27 is elongated and in the illustrated embodiment is suitably hollow (FIGS. 3 and 5) so that the withdrawal string 29 attached to the tampon 25 can extend out through an outer end 65 of the plunger. It is understood though that the plunger 27 need not be hollow, and that the withdrawal string 29 may extend other than through the plunger without departing from the scope of this invention. A substantial length of the plunger 27, extending to the outer end 65 thereof, is accessible exterior of the barrel 23 in the extended position of the plunger for gripping by the user to move the plunger relative the barrel. The plunger has an increased outer diameter adjacent its outer end 65, such as in the form of a flange, ring, bell-shape as in the illustrated embodiment or other suitable shape to facilitate gripping the plunger and to act as a stop to inhibit the outer end of the plunger against entering the barrel 23.

In accordance with one embodiment, the barrel 23 is constructed such that the outer surface of the barrel at least at the central region 43 thereof, and more suitably at both the central region and the tip region 45 of the barrel, has a relatively low coefficient of friction to facilitate comfortable insertion of the barrel into the vaginal canal and removal therefrom. The barrel 23 is additionally constructed such that the outer surface of the barrel at its grip region 41 has a coefficient of friction that is substantially greater than the coefficient of friction at the central region 43 and tip region 45 of the barrel to facilitate gripping of the barrel while still providing a comfortable engagement between the outer surface of the barrel and the vaginal canal. Still more suitably, the barrel 23 is constructed to have a relatively soft feel and appearance while also providing the coefficient of friction differential between the grip region 41 and the central and tip regions 43, 45 of the barrel.

Generally speaking, frictional forces occur between any two contacting bodies where there are forces tending to slide one of the bodies relative to the other. The frictional forces act parallel to the contacting surfaces and opposite the forces tending to cause sliding between the bodies. Further, the frictional forces are proportional to normal forces on the bodies and to the tendency of the bodies to grip each other.

As used herein, the coefficient of friction is the ratio of the frictional force between the bodies to the normal force between the bodies. The coefficient of friction is different between bodies at rest and bodies moving relative to each other. In general, two bodies contacting one another, but not moving relative to one another, will exhibit greater frictional resistance to motion than bodies that are moving relative to one another. Hence, a static coefficient of friction (i.e., a coefficient of friction between bodies which are not moving relative to each other) may but need not necessarily be somewhat greater than a dynamic coefficient of friction (i.e., a coefficient of friction between bodies which are moving relative to each other). Larger coefficients of friction correspond to larger amounts of friction between bodies, while smaller frictional coefficients correspond to smaller amounts of friction. As used further herein, the term coefficient of friction refers to at least one of a static coefficient friction and a dynamic coefficient of friction. In particularly suitable embodiments, the coefficient of friction differential described previously is present for both static and dynamic coefficients of friction.

As one example, the barrel 23 according to one embodiment may be suitably constructed of at least two materials that differ in at least one characteristic. More suitably, in one embodiment the barrel is constructed of a first material that comprises the tip region 45, central region 43 and an underlying portion of the grip region 41, and a second material that comprises the overlying portion of the grip region. For example, the barrel 23 may be constructed along its full length (i.e., at the tip region 45, central region 43 and grip region 41) of a polymeric first or core layer 81 comprising a polyolefin such as, without limitation, polypropylene, polyethylene, low density polyethylene, high density polyethylene, linear low density polyethylene, near low density polyethylene, polyethylene terephthalate PET), nylon, polystyrene, polyvinyl chloride, polymethyl methacrylate, polyolefin elastomer, copolymers of alfa-olefines, and combinations thereof. More suitably the first or core layer 81 of the barrel 23 is formed of a low density polyethylene or a polymeric blend that includes low density polyethylene, such as a combination of low density polyethylene and at least one of linear low density polyethylene or a high density polyethylene.

One or more additives may be added to the polymeric first layer 81 of the barrel 23 (prior to molding) to enhance the slip characteristic (e.g., to provide a low coefficient of friction) of the barrel outer surface at least at the central region 43 of the barrel and more suitably at the central region and tip region 45 of the barrel. For example, suitable such additives include without limitation erucamide, demethicone, oleamide, fatty acid amide and combinations thereof. It is understood that other additives may used to provide enhanced slip characteristics to the barrel 23 outer surface without departing from the scope of this invention. In other embodiments the barrel 23 may instead, or additionally, be coated with a friction reducing, or slip agent such as, without limitation, wax, polyethylene, silicone, cellophane, clay and combinations thereof. In still other suitable embodiments the barrel 23 may comprise a polymer blend melted together and co-extruded to provide a low coefficient of friction.

In the illustrated embodiment, the barrel 23 is further constructed so that the barrel outer surface at the tip region 45 has a lower coefficient of friction than at the central region 43 of the barrel to facilitate easier insertion of the barrel, inner end first, into the vaginal canal. This is particularly useful on days which a period is relatively light. For example, the outer surface of the barrel 23 at the tip region 45 may be configured to have a substantially lower surface roughness than at the central region 43 of the barrel, and more suitably the tip region may be substantially smooth or polished to reduce the coefficient of friction of the tip region relative to that of the central region. As a particular example, the surface roughness (which provides a tactile perception to the user) of the central region 43 of the barrel may have a surface roughness of less than or equal to about 36 and is more suitably about 27 in accordance with VDI Richtlinie [Standard] 3400. VDI Richtlinie 3400 has the German title: "Electroerosive Bearbeitung, Begriffe, Verfahren, Anwendung" [Electrical Discharge Machining, Definitions, Process, Application], published by the Verein Deutscher Ingenieure [Association of German Engineers] in June 1975.

In another embodiment, the first or core layer 81 is constructed of at least two different but generally compatible materials (e.g., so that the barrel 23 is comprised of at least three materials—including the material from which the grip region 41 is constructed). In one particular such embodiment, the central region 43 and the tip region 45 of the barrel 23 are of different materials. The material from which the central region 43 is formed may also form an underlying layer of the grip region 41 and a third material forms an overlying or outer layer of the grip region. As an example, one suitable process for making the first or core layer 81 of at least two different materials as described above is referred to as a coinjection process and more particularly a sequential coinjection process. Such injection processes are known to those skilled in the art for molding together two compatible polymer melts.

In a sequential coinjection process, the material injected first (e.g., the material from which the tip region 45 is formed) flows to the wall near the entrance to the mold, and the second material (e.g., the material from which the central region 43—and underlying portion of the grip region 41 is formed) then enters the mold and continues to flow in the center of the channel and fan out to the wall further down the part. In this way the far end of the part, e.g., the tip region 45, can be comprised solely of the first material, while the portion of the barrel 23 forming the grip region 41 and central region 43, will contain the stiffer second material. To obtain stable and uniform skin layer thickness, it is preferred that the first material, have a lower viscosity than the second material. Having a lower viscosity ratio for the first material compared to the second material will also help the first material to be packed into the tip region 45.

One benefit of using sequential coinjection is that it provides more control over the composition of the part. The relative amounts of soft polymer (for the tip region 45) and stiffer polymer (for the central region 43) can be varied to control the flexibility/stiffness balance of the part. For example, a larger fraction of stiff polymer can be used to increase the overall stiffness of the part as compared to two-shot or multishot injection processes, in which the amounts of each region are fixed by the mold dimensions, or compared to single injection processes where the entire part is the same composition. Sequential coinjection also provides a seamless transition between regions, because there is no interface between materials on the surface of the part.

In other embodiments, the tip region 45 of the barrel 23 may instead, or additionally be coated with a friction reducing agent so that the outer surface of the barrel at the tip region has a lower coefficient of friction than that of the central region of the barrel. Providing a surface roughness differential between the tip region 45 and the central region 43 also serves as a visual indicator of the reduced friction coefficient at the tip region.

The grip region 41 is suitably constructed of a second or skin layer 83 applied over the first or core layer 81 along a longitudinal segment of the barrel 23 generally at the grip region thereof. In one particularly suitable embodiment, the second, or skin layer 83 forming the grip region 41 may comprise a thermoplastic elastomer (TPE) to provide the grip region with a soft, relatively rubbery feel that has a higher coefficient of friction than the first, or core layer 81 that defines the outer surface of at least the central region 43 of the barrel 23. It is understood, however, that other suitable materials may be used as the second, or skin layer 83 to provide a higher coefficient of friction to the grip region 41 without departing from the scope of this invention.

In other embodiments, the central region 43 and the grip region 41 may also be of different colors, which as used herein includes different hues as well as different shades of the same color as long as the different colors are visually perceptible by a human adult having 20/20 vision. Such a color change provides a visual cue to the user of a characteristic difference between the central region 43 and the tip region 45.

In the illustrated embodiment of FIG. 1, a visual indicator, indicated generally at 91, is provided at the grip region 41 to facilitate identification by the user of the grip region location. The visual indicator 91 in FIG. 1, for example, comprises a flower pattern formed in the grip region 43 to identify the grip region. More particularly, an underlying set of flower petals is formed as part of the first or core layer 81 of the barrel 23 during molding. The second or skin layer 83 of the barrel 23 at the grip region 41 has openings therein corresponding to and aligned with the molded flower petals so that the flower petals are visually perceptible through the second or skin layer of the barrel. More suitably, the flower petals are of a different color (such as by being the same color as the central region 43 of the barrel 23) than the second or skin layer 83 that defines the grip region 41.

It is understood that the visual indicator 93 may be formed other than integrally with the barrel 23 during initial molding of the barrel, such as by imprinting the visual indicator on the barrel at the grip region (e.g., a textual message or a suitable image) without departing from the scope of this invention. It is also understood that a visual indicator 91 (other than the different material and/or color of the second or skin layer 83) may be omitted from the grip region 41.

The applicator plunger 27 is, in one particularly suitable embodiment, constructed of the same material (e.g., polymer or polymer blend) as at least the first layer 81 (FIG. 2, e.g., the central region 43 and/or tip region 45) of the barrel to provide a relatively low coefficient of friction to plunger for sliding within the guide channel 63. While not shown in the drawings, it is contemplated that the plunger 27 may also be formed by a coinjection process similar to that used to form the barrel 23 so that a second or skin layer is applied to the plunger, such as at or adjacent the outer end 65 of the plunger to facilitate enhanced gripping of the plunger during use. It is also contemplated that the end of the plunger 27 may be constructed to have a relatively smooth or polished outer surface and as such have a different surface roughness and/or visual appearance than the rest of the plunger as illustrated in FIG. 1.

Figure 6:
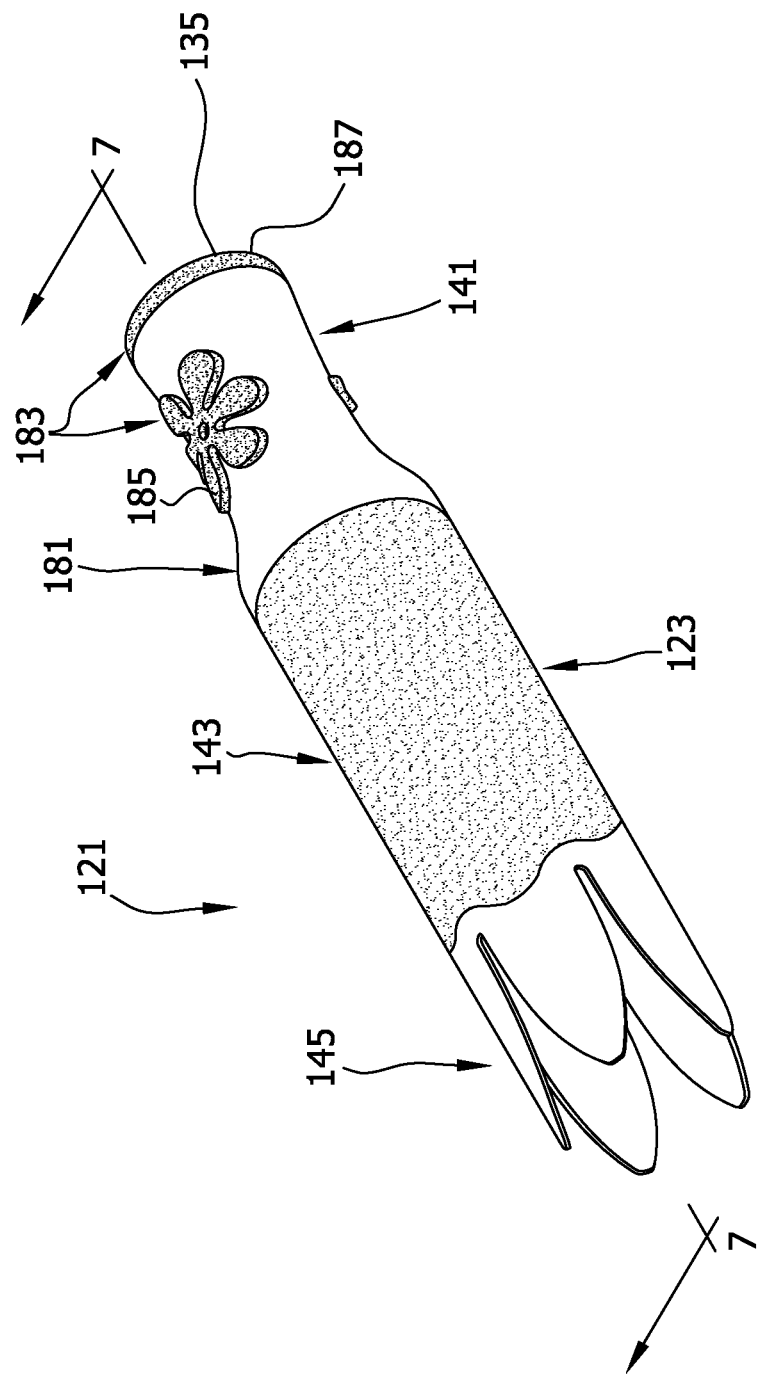
FIG. 6 is a perspective view of a second embodiment of a tampon applicator, with a plunger of the applicator illustrated in an extended position relative to a barrel of the applicator and with a tip of the barrel open to illustrate construction of the barrel.
Figure 7:
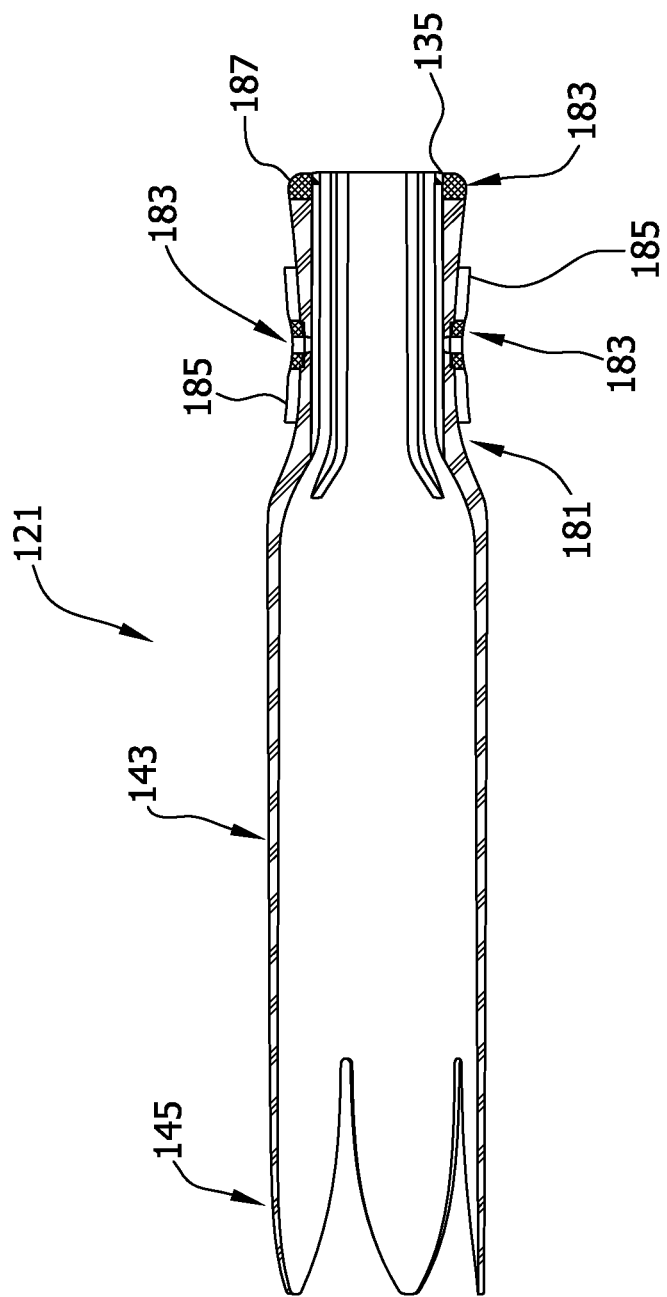
FIG. 7 is a longitudinal cross-section taken in the plane of line 7-7 of FIG. 6.

FIGS. 6 and 7 illustrate a barrel 123 of a second embodiment of a tampon applicator 121. In this second embodiment, the central region 143 and tip region 145 of the barrel are substantially the same as that of the embodiment of FIGS. 1-5. At the grip region 141 of the barrel 123 of this second embodiment the second or skin layer 183 itself is in the form of a raised flower pattern 185 (or other suitable pattern) and/or as a ring or collar 187 adjacent the outer end 135 of the barrel. A corresponding pattern is recessed into the outer surface of the first or core layer 181 during molding and the patterned second or skin layer 183 is applied to the first or core layer to generally seat in the recessed pattern and extend transversely outward of the first layer to provide a higher coefficient of friction layer at the grip region 141. In this manner, the second or skin layer 183 in the form of a flower pattern also acts as a visual indicator of the grip region 141 location. It is understood that the second or skin layer 183 may be any suitable pattern other than a flower pattern, or other suitable raised surface, without departing from the scope of this invention.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above products without departing from the scope of the invention, it is intended that all matter contained in the above description and shown in the accompanying drawings shall be interpreted as illustrative and not in a limiting sense.

What is claimed is:

1. A tampon applicator comprising:
    an elongated barrel having an interior chamber for housing a tampon therein, an outer end and an inner end spaced longitudinally from the outer end; and
    a plunger extending into the barrel at the outer end thereof and moveable relative to the barrel to expel the tampon from the barrel at the inner end of the barrel;
    the barrel having at least two petals each having a base and extending longitudinally of the barrel to a tip of the petal wherein the petal tips define the longitudinal inner end of the barrel, the petals being configurable relative to each other and to the barrel from a closed configuration in which the petals generally close the inner end of the barrel and an opened position in which the petals are moved generally transversely outward to form an exit opening at the inner end of the barrel upon movement of the plunger to expel the tampon from the barrel at said inner end, each petal having a length from its base to its tip, the barrel having a cross-sectional dimension at the bases of said petals, a ratio of the length of said petal to the cross-sectional dimension of the barrel at the bases of said petals being in the range of about 1.0 to about 2.0.

2. The tampon applicator set forth in claim 1 wherein the ratio of the length of said petal to the cross-sectional dimension of the barrel at the bases of said petals is in the range of about 1.0 to about 1.5.

3. The tampon applicator set forth in claim 1 wherein the ratio of the length of said petal to the cross-sectional dimension of the barrel at the bases of said petals is in the range of about 1.0 to about 1.25.

4. The tampon applicator set forth in claim 1 in combination with a tampon housed within the interior chamber of the applicator barrel, the tampon extending longitudinally within the interior chamber and having an inner end in opposed relationship with the inner end of the barrel in the closed configuration of the petals and spaced longitudinally from the inner end of the barrel a distance in the range of about 0.1 mm to about 1.5 mm.

5. The tampon applicator and tampon set forth in claim 4 wherein the inner end of the tampon is spaced longitudinally from the inner end of the barrel a distance in the range of about 0.1 mm to about 0.4 mm.

6. The tampon applicator set forth in claim 1 wherein the barrel has a tip region defined at least in part by said petals and a central region longitudinally adjacent the tip region and at least in part defining the interior chamber of the barrel, the barrel having an outer surface, the outer surface of the barrel at the tip region of the barrel being different from the outer surface of the barrel at the central region thereof visually and further being different from the outer surface of the barrel in at least one of tactile perception and coefficient of friction.

7. The tampon applicator set forth in claim 6 wherein a coefficient of friction of the barrel outer surface at said tip region is less than a coefficient of friction of the barrel outer surface at said central region.

8. A tampon applicator comprising:
    an elongated barrel having an interior chamber for housing a tampon therein, an outer end and an inner end spaced longitudinally from the outer end; and
    a plunger extending into the barrel at the outer end thereof and moveable relative to the barrel to expel the tampon from the barrel at the inner end of the barrel;
    the barrel having a guide channel extending longitudinally therein adjacent the outer end of the barrel, the plunger extending through the guide channel into the interior chamber of the barrel, the guide channel having a cross-sectional dimension sized for a sliding friction fit of with the plunger, said guide channel further having a length, a ratio of the length of the guide channel to the cross-sectional dimension thereof being in the range of about 1 to about 5.

9. The tampon applicator set forth in claim 8 wherein the ratio of the length of the guide channel to the cross-sectional dimension thereof is in the range of about 2 to about 4.

10. The tampon applicator set forth in claim 8 wherein the guide channel length is in the range of about 3 to about 3.5 mm.

11. The tampon applicator set forth in claim 8 wherein applicator barrel has a grip region at least in part corresponding to the guide channel, a central region longitudinally adjacent the grip region and at least in part defining the interior chamber for housing the tampon within the barrel, and an outer surface, the outer surface of the barrel at the grip region of the barrel being different from the outer surface of the barrel at the central region thereof in at least one of color, material of construction and coefficient of friction.

12. The tampon applicator set forth in claim 11 wherein the barrel outer surface at the grip region of the barrel has a coefficient of friction that is substantially greater than the barrel outer surface at the central region of said barrel.

13. The tampon applicator set forth in claim 11 wherein the grip region of the barrel comprises a thermoplastic elastomer.

14. The tampon applicator set forth in claim 11 wherein the applicator barrel further has a tip region longitudinally spaced from the grip region by the central region of the barrel, the outer surface of the barrel at the grip region of the barrel being different from the outer surface of the barrel at the tip region thereof in at least one of color, material of construction and coefficient of friction.

15. The tampon applicator set forth in claim 14 wherein the barrel outer surface at the grip region of the barrel has a coefficient of friction that is substantially greater than the barrel outer surface at the tip region of said barrel.

16. A tampon applicator comprising:
   an elongated barrel having an interior chamber for housing a tampon therein, an outer end, an inner end spaced longitudinally from the outer end, a grip region generally adjacent the outer end of the barrel, a tip region generally adjacent the inner end of the barrel, a central region extending longitudinally between the grip region and the tip region, and an outer surface; and
   a plunger extending into the barrel at the outer end thereof and moveable relative to the barrel to expel the tampon from the barrel at the inner end of the barrel;
   the outer surface of the barrel at the grip region having at least one of a different color and a different coefficient of friction than the central region of the barrel, the outer surface of the barrel at the central region having a surface roughness less than or equal to about 36 in accordance with VDI Richtlinie [Standard] 3400.

17. The tampon applicator set forth in claim 16 wherein the outer surface of the barrel at the grip region has a coefficient of friction substantially greater than the coefficient of friction of the outer surface of the barrel at the central region thereof.

18. The tampon applicator set forth in claim 16 wherein the grip region of the barrel is constructed at least in part of a different material than the central region of the barrel.

19. The tampon applicator set forth in claim 18 wherein the grip region of the barrel is constructed at least in part of a thermoplastic elastomer.

20. The tampon applicator set forth in claim 16 wherein the outer surface of the barrel at the grip region has at least one of a different color and a different coefficient of friction than the tip region of the barrel.

21. The tampon applicator set forth in claim 20 wherein the coefficient of friction of the outer surface of the barrel at the grip region is substantially greater than the coefficient of friction of the outer surface of the barrel at the tip region thereof.

22. The tampon applicator set forth in claim 16 wherein the barrel at the tip region thereof is different from the barrel at the central region thereof in visual appearance and at least one of tactile perception, outer surface coefficient of friction and stiffness.

23. The tampon applicator set forth in claim 22 wherein the coefficient of friction of the barrel outer surface at said tip region is less than the coefficient of friction of the barrel outer surface at said central region.

24. The tampon applicator set forth in claim 16 further comprising a grip indicator at said grip region configured to provide a visual cue to the user of the location of said grip region.

* * * * *